US012727840B2

(12) United States Patent
Ishitsu

(10) Patent No.: US 12,727,840 B2
(45) Date of Patent: Sep. 8, 2026

(54) X-RAY IMAGING APPARATUS

(71) Applicant: FUJIFILM Healthcare Corporation, Chiba (JP)

(72) Inventor: Takafumi Ishitsu, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 138 days.

(21) Appl. No.: 18/770,636

(22) Filed: Jul. 11, 2024

(65) Prior Publication Data

US 2025/0025122 A1 Jan. 23, 2025

(30) Foreign Application Priority Data

Jul. 20, 2023 (JP) ................................ 2023-117922

(51) Int. Cl.
*A61B 6/00* (2024.01)
*A61B 6/42* (2024.01)
*G01T 1/24* (2006.01)

(52) U.S. Cl.
CPC .............. *A61B 6/54* (2013.01); *A61B 6/4241* (2013.01); *G01T 1/241* (2013.01)

(58) Field of Classification Search
CPC ......... A61B 6/54; A61B 6/4241; A61B 6/542; A61B 6/032; A61B 6/035; A61B 6/0407; A61B 6/06; G01T 1/241
See application file for complete search history.

(56) References Cited

U.S. PATENT DOCUMENTS

2013/0343517 A1* 12/2013 Gagnon ................. A61B 6/032 378/19
2023/0414187 A1* 12/2023 Haider ................. A61B 6/4411

FOREIGN PATENT DOCUMENTS

JP 2021194354 12/2021

* cited by examiner

*Primary Examiner* — Kiho Kim
(74) *Attorney, Agent, or Firm* — JCIPRNET

(57) ABSTRACT

Provided is an X-ray imaging apparatus capable of stabilizing polarization of a photon counting detector and suppressing ineffective exposure of a subject. An X-ray imaging apparatus comprises an X-ray source that irradiates an X-ray, a photon counting detector that counts an X-ray photon for each energy bin, and an image generation unit that generates a medical image of a subject based on a detector output from the photon counting detector. The X-ray imaging apparatus further comprises a control unit that checks, in a case where polarization of the photon counting detector is not stable, the subject not being present in an X-ray irradiation field which is a range where the X-ray is irradiated from the X-ray source and then causes the X-ray source to irradiate the photon counting detector with the X-ray.

11 Claims, 4 Drawing Sheets

X-RAY IMAGING APPARATUS

CLAIM OF PRIORITY

The present application claims priority from Japanese Patent Application JP 2023-117922 filed on Jul. 20, 2023, the content of which is hereby incorporated by reference into this application.

BACKGROUND OF THE INVENTION

1. Field of the Invention

The present invention relates to an X-ray imaging apparatus comprising a photon counting detector, and particularly to a technique of suppressing an influence of polarization of a photon counting detector.

2. Description of the Related Art

Development of a photon counting computed tomography (PCCT) apparatus is in progress as an X-ray imaging apparatus comprising a photon counting detector that is a detector employing a photon counting method. Since the photon counting detector can measure energy of an X-ray photon, the PCCT apparatus can present a medical image including more information than a medical image of a CT apparatus in the related art, for example, a medical image divided into a plurality of energy bins.

In the photon counting detector that is in a state where imaging is possible by applying a voltage, polarization progresses according to a length of time the voltage is applied, and a wave height value of a detector output gradually decreases. A change in the wave height value of the detector output causes an error in the energy of the X-ray photon to be measured, and adversely affects image quality of the medical image divided into the energy bins.

JP2021-194354A discloses an X-ray imaging apparatus that determines, to suppress an influence of polarization of a photon counting detector, whether or not the polarization of the photon counting detector applied with a high voltage is stable and starts data collection in a case where the polarization is stable.

SUMMARY OF THE INVENTION

However, in JP2021-194354A, there is no consideration for the progress of polarization caused by X-ray irradiation. The polarization of the photon counting detector progresses not only by applying the high voltage but also by the X-ray irradiation. To image a subject after stabilizing the polarization due to the X-ray irradiation, the X-ray irradiation to the photon counting detector is required to be executed immediately before the imaging. Further, ineffective exposure of the subject to the X-ray irradiated to the photon counting detector is required to be suppressed.

Therefore, an object of the present invention is to provide an X-ray imaging apparatus capable of stabilizing polarization of a photon counting detector and suppressing ineffective exposure of a subject.

In order to achieve the above object, according to an aspect of the present invention, there is provided an X-ray imaging apparatus comprising an X-ray source that irradiates an X-ray, a photon counting detector that counts an X-ray photon for each energy bin, and an image generation unit that generates a medical image of a subject based on a detector output from the photon counting detector, in which the X-ray imaging apparatus further comprises a control unit that checks, in a case where polarization of the photon counting detector is not stable, the subject not being present in an X-ray irradiation field which is a range where the X-ray is irradiated from the X-ray source and then causes the X-ray source to irradiate the photon counting detector with the X-ray.

According to the present invention, it is possible to provide the X-ray imaging apparatus capable of stabilizing the polarization of the photon counting detector and suppressing the ineffective exposure of the subject.

DESCRIPTION OF THE PREFERRED EMBODIMENTS

Hereinafter, embodiments of the present invention will be described with reference to drawings. An X-ray imaging apparatus according to the embodiment of the present invention is applied to an apparatus comprising an X-ray source and a photon counting detector. In the following description, an example will be described in which the X-ray imaging apparatus is an X-ray CT apparatus.

Example 1

Figure 1:
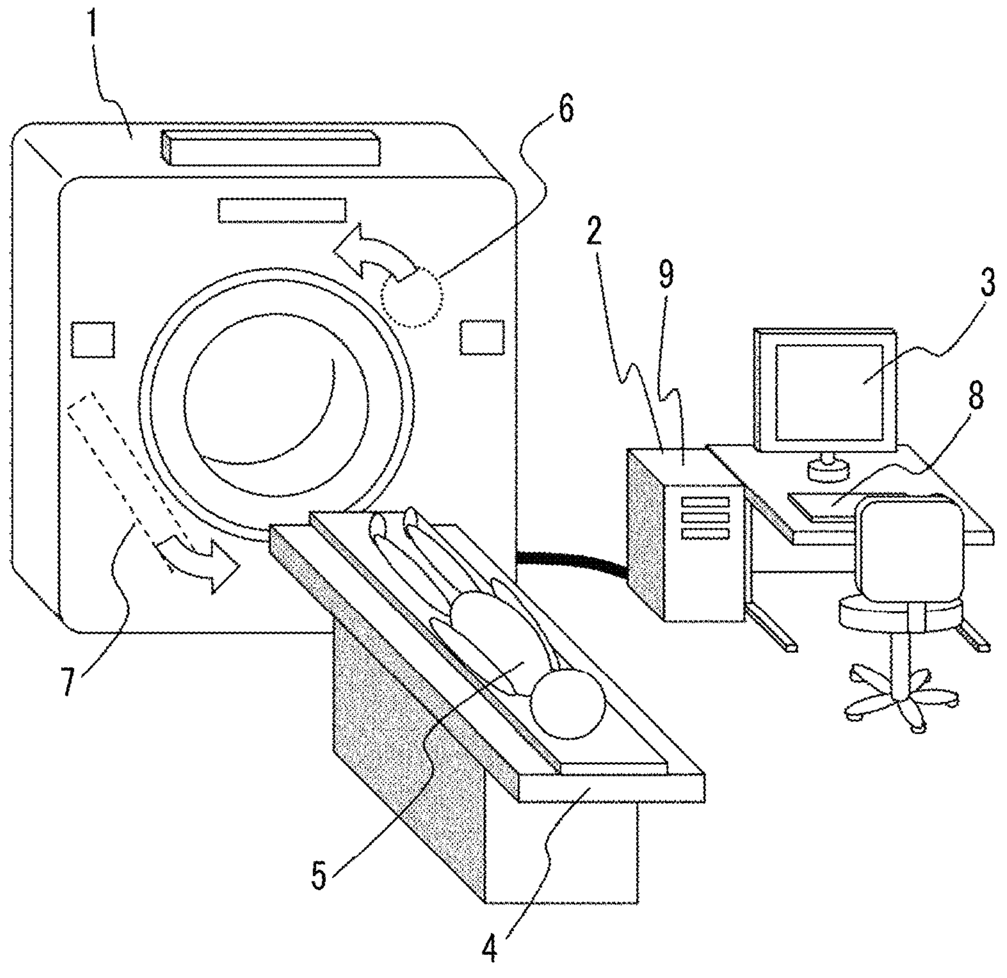
FIG. 1 is a diagram showing an overall configuration of an X-ray CT apparatus of Example 1.

FIG. 1 is an overall configuration diagram of an X-ray CT apparatus according to the present example. The X-ray CT apparatus comprises a gantry 1, a calculation device 2, a display device 3, and a bed 4, counts an X-ray photon absorbed by a subject 5 placed on the bed 4, and generates a tomographic image of the subject 5 based on the number of counts. Hereinafter, each unit will be described.

The gantry 1 includes a rotation portion that is mounted with an X-ray tube 6 and a detector panel 7 and that rotates, and a stationary portion that supports the rotation portion. The X-ray tube 6 is an X-ray source that hits a target with an electron accelerated at a high voltage of about 100 kV to generate an X-ray. The detector panel 7 is a photon counting detector that is disposed to face the X-ray tube 6 with the subject 5 interposed therebetween, counts the X-ray photon transmitted through the subject 5, and measures a spatial distribution of the number of X-ray photons. The number of X-ray photons transmitted through the subject 5 is subtracted from the number of X-ray photons in a case where the subject 5 is not present to obtain the number of X-ray photons absorbed by the subject 5, which is acquired as projection data. Since the detector panel 7 is the photon counting detector and can measure energy of the X-ray photon, the projection data for each energy bin is acquired. A detailed structure of the detector panel 7 will be described below with reference to FIG. 2.

While the X-ray tube 6 and the detector panel 7 rotate around the subject 5, X-ray irradiation to the subject 5 by the X-ray tube 6 and the counting of the X-ray photon by the detector panel 7 are repeated, and thus the projection data of the subject 5 is acquired in various directions. The projection data is acquired by approximately 3,000 frames in one second and is transmitted to the calculation device 2. The bed 4 is horizontally moved toward an opening portion of the gantry 1 to adjust a position of the subject 5 at which projection data is acquired.

The calculation device 2 has the same hardware configuration as a general computer device, comprises a central processing unit (CPU), a memory, or the like, and is connected to the display device 3, an input device 8, and a storage device 9. The calculation device 2 generates the tomographic image by image reconstruction using a plurality of projection data to be transmitted and controls each unit. For example, the calculation device 2 controls a voltage applied to the X-ray tube 6, a rotation speed of the X-ray tube 6 and the detector panel 7, or the like.

The display device 3 is a liquid crystal display, a touch panel, or the like, and displays the generated tomographic image or the like. The input device 8 is a keyboard, a mouse, or the like, and is used for setting the voltage applied to the X-ray tube 6 or the like. In a case where the display device 3 is the touch panel, the touch panel functions as the input device 8. The storage device 9 is a hard disk drive (HDD), a solid state drive (SSD), or the like, and stores various types of data such as a program executed by the CPU, the projection data, and the tomographic image.

Figure 2:
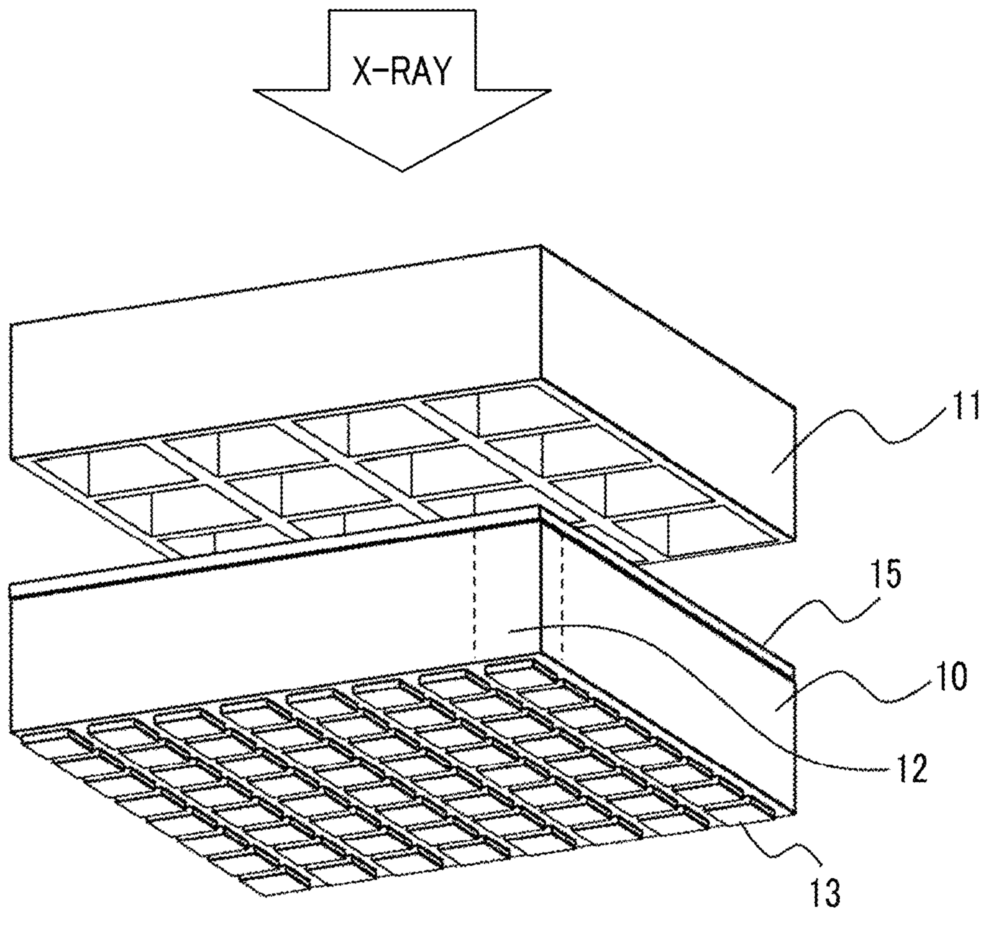
FIG. 2 is a diagram showing a configuration of a detector panel of Example 1.

An example of the detector panel 7 will be described with reference to FIG. 2. The detector panel 7 includes an X-ray detector 10 and a collimator 11, and is provided in the rotation portion of the gantry 1.

The X-ray detector 10 is a semiconductor detector that detects the X-ray photon transmitted through the subject 5. The X-ray detector 10 uses CdTe or CdZnTe. A high voltage electrode 15 is provided on a side on which the X-ray is incident, and a plurality of readout electrodes 13 are provided on an opposite side. A negative high voltage is applied to the high voltage electrode 15 with respect to the readout electrode 13, which is a ground voltage, and an electric field is formed between the high voltage electrode 15 and the readout electrode 13. In a case where the X-ray photon is incident on the X-ray detector 10, the number of electrons and holes according to the energy of the X-ray photon are generated. The electron generated by the incidence of the X-ray photon moves to a nearest readout electrode 13 by the electric field between the electrodes and is read out as an electric signal. That is, the readout electrode 13 corresponds to a detection pixel 12 of the X-ray detector 10.

The collimator 11 is a metal grid having a plurality of holes and is provided in a front of the X-ray detector 10 to suppress incidence of a scattered ray, which is generated from the subject 5 and the like, into the X-ray detector 10. The collimator 11 uses a metal having a large density and atomic number, such as tungsten or molybdenum, and the holes of the collimator 11 are aligned with positions corresponding to the detection pixels 12.

Figure 3A:
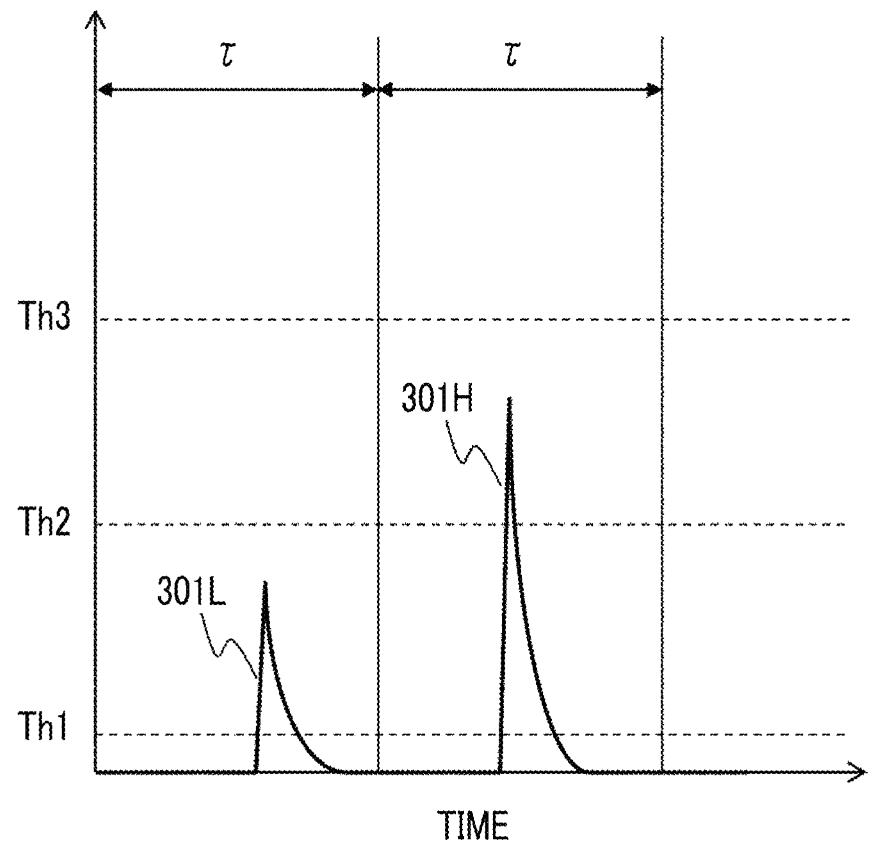
FIGS. 3A and 3B are diagrams for describing an influence of polarization.
Figure 3B:
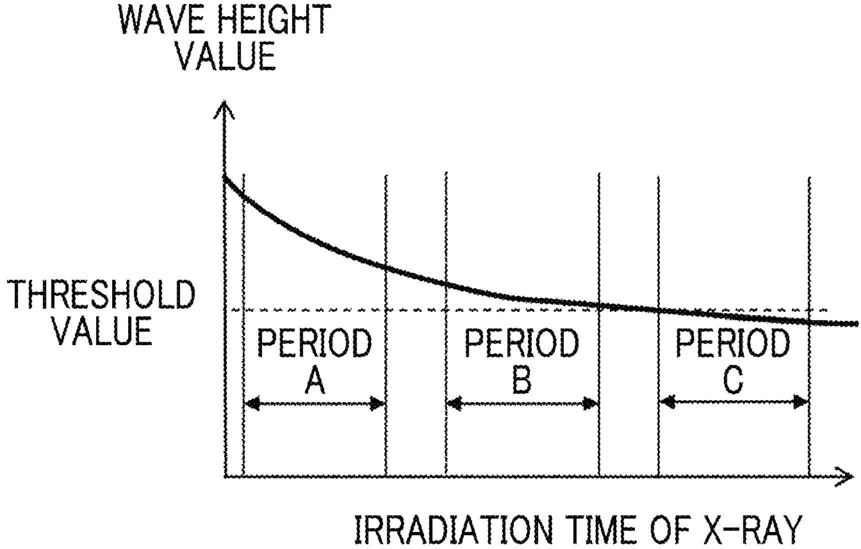

An influence of polarization of the X-ray detector 10 will be described with reference to FIGS. 3A and 3B. FIG. 3A is an example of an output waveform generated in a case where the X-ray photon is incident on the X-ray detector 10, in which the horizontal axis is time and the vertical axis is a detector output. Further, FIG. 3B is an example of an attenuation curve which is a temporal change of a wave height value of the output waveform, in which the horizontal axis is an irradiation time of the X-ray and the vertical axis is a wave height value of the detector output.

In the photon counting detector, a pulse output 301 is generated each time the X-ray photon is incident in a dead time $\tau$, and the wave height value of the pulse output 301 is proportional to photon energy. FIG. 3A illustrates a pulse output 301L in a case where the photon energy of the incident X-ray photon is relatively low and a pulse output 301H in a case where the photon energy thereof is relatively high. That is, the detector output is classified into threshold values Th1, Th2, Th3, and the like to discriminate the X-ray photon for each photon energy bin.

However, in a case where the X-ray detector 10 is continuously irradiated with the X-ray, the electron or the hole is trapped inside the X-ray detector 10, and the polarization progresses with elapse of the irradiation time of the X-ray. Since the polarization delays the movement of the electron or the hole, a part of the electron generated between the electrodes cannot reach the readout electrode 13 within the dead time $\tau$, and the wave height value decreases as the irradiation time increases as shown in FIG. 3B. That is, even in a case where the X-ray photons having the same photon energy are incident, the wave height value is different. Therefore, an error occurs in the energy of the X-ray photons to be measured. An amount of change in the wave height value is largest immediately after the X-ray is irradiated, for example, in a period A of FIG. 3B, and is decreased as time progresses from a period B to a period C. That is, the polarization of the X-ray detector 10 is stabilized as the irradiation time of the X-ray elapses.

In Example 1, the X-ray is irradiated immediately before the imaging of the subject to stabilize the polarization of the X-ray detector 10. In a case where the polarization progresses excessively, characteristics of the X-ray detector 10 deteriorate, and an increase in noise, a decrease in a counting rate, or the like occurs. Thus, the irradiation of the X-ray is desirably stopped in a period in which the wave height value is equal to or higher than a predetermined threshold value, for example, the period B instead of the period C in FIG. 3B.

Figure 4:
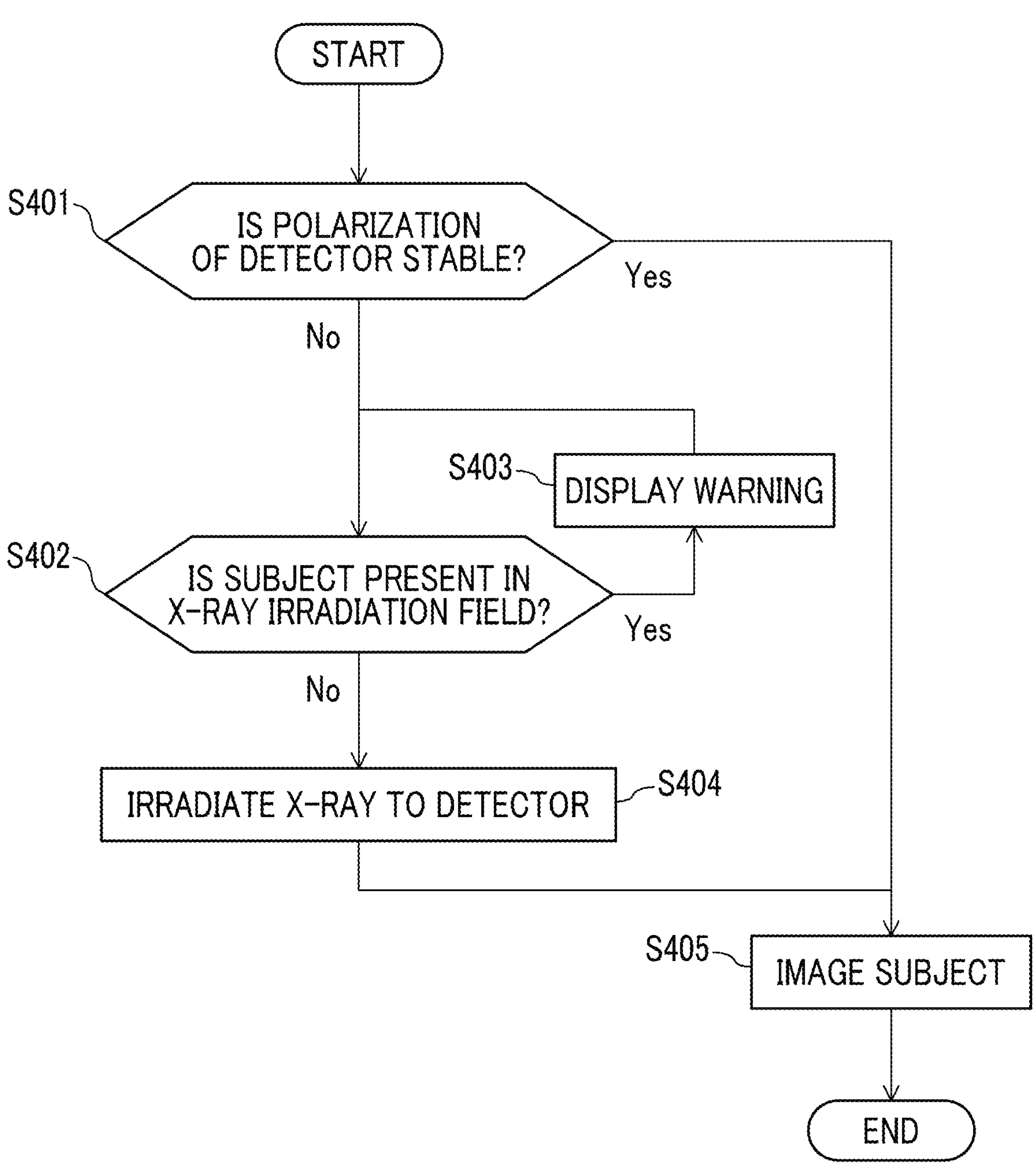
FIG. 4 is a diagram showing an example of a flow of processing of Example 1.

A flow of processing of Example 1 will be described with reference to FIG. 4.

S401

The calculation device 2 determines whether the polarization of the X-ray detector 10 is stable. In a case where the polarization is not stable, the processing proceeds to S402. In a case where the polarization is stable, the processing proceeds to S405.

Whether or not the polarization of the X-ray detector 10 is stable is determined, for example, based on an elapsed time from previous imaging. That is, in a case where the elapsed time from the previous imaging is shorter than a predetermined time, the polarization is determined to be stable. With the determination based on the elapsed time from the previous imaging, it is possible to determine whether the polarization is stable by simple processing. The predetermined time is set in advance based on a result of a pre-measurement, and for example, 10 minutes is set. Since the polarization progresses as an irradiation dose is larger, the predetermined time is set in accordance with the irradiation dose. With the setting of the predetermined time in accordance with the irradiation dose, it is possible to more accurately determine whether the polarization is stable.

S402

The calculation device 2 determines whether the subject 5 is present in an X-ray irradiation field. The X-ray irradiation field is a range in which the X-ray is irradiated from the X-ray tube 6. In a case where the subject 5 is not present in the X-ray irradiation field, the processing proceeds to S404. In a case where the subject 5 is present in the X-ray irradiation field, the processing returns to S402 via S403.

Whether or not the subject 5 is present in the X-ray irradiation field is determined, for example, based on a position of the bed 4. That is, in a case where the bed 4 is present in the X-ray irradiation field, the subject 5 is determined to be present in the X-ray irradiation field. With the determination based on the position of the bed 4, it is possible to determine the presence or absence of the subject 5 without adding new hardware.

Further, whether the subject 5 is present in the X-ray irradiation field may be determined based on an image of a camera that images the X-ray irradiation field. That is, in a case where the image of the camera includes the subject 5, the subject 5 is determined to be present in the X-ray irradiation field. With the determination based on the image of the camera, it is possible to determine the presence or absence of the subject 5 even in a case where the subject 5 protruding from the bed 4 is present in the X-ray irradiation field.

Further, whether the subject 5 is present in the X-ray irradiation field may be determined based on an image obtained by low-dose imaging. The low-dose imaging uses an X-ray dose lower than an X-ray dose irradiated from the X-ray tube 6 in a case where a medical image of the subject 5 is captured. That is, in a case where the image obtained by the low-dose imaging includes the subject 5, the subject 5 is determined to be present in the X-ray irradiation field. With the determination based on the image of the low-dose imaging, it is possible to determine the presence or absence of the subject 5 without adding new hardware even in a case where the subject 5 protruding from the bed 4 is present in the X-ray irradiation field.

S403

The calculation device 2 causes the display device 3 to display a message for warning that the subject 5 is present in the X-ray irradiation field. The processes of S402 and S403 are repeated until an operator operates the bed 4 to retreat the subject 5 from the X-ray irradiation field in response to the message displayed on the display device 3. In a case where the number of times of repetition of the processes of S402 and S403 reaches a predetermined threshold value, the flow of the processing may be ended. Further, in S403, the calculation device 2 may control the bed 4 to retreat the subject 5 from the X-ray irradiation field.

S404

The calculation device 2 controls the X-ray tube 6 to irradiate the X-ray to the X-ray detector 10. The irradiation time of the X-ray is a preset length and may be set in accordance with the irradiation dose.

S405

The calculation device 2 controls the gantry 1 and the bed 4 to image the subject 5. That is, the bed 4 is moved into the gantry 1 and the X-ray irradiation and the counting of the X-ray photon are repeated while rotating the X-ray tube 6 and the detector panel 7 around the subject 5 to acquire the projection data from various directions. With the image reconstruction using the plurality of projection data, the tomographic image is generated as the medical image.

With the flow of the processing described with reference to FIG. 4, it is possible to stabilize the polarization of the photon counting detector and to suppress the ineffective exposure of the subject 5. That is, since it is checked that the subject 5 is not present in the X-ray irradiation field and then the X-ray is irradiated to stabilize the polarization of the photon counting detector, it is possible to suppress the ineffective exposure of the subject 5. Further, since the polarization of the photon counting detector is stabilized by the irradiation of the X-ray and then the subject 5 is captured, it is possible to keep the image quality of the medical image from being adversely affected.

The X-ray imaging apparatus according to the embodiment of the present invention is not limited to the above-described examples, and the components can be modified and embodied without departing from the scope of the present invention. Further, a plurality of components disclosed in the above-described examples may be combined as appropriate. Further, some components may be deleted from all the components described in the above-described examples.

EXPLANATION OF REFERENCES

- 1: gantry
- 2: calculation device
- 3: display device
- 4: bed
- 5: subject
- 6: X-ray tube
- 7: detector panel
- 8: input device
- 9: storage device
- 10: X-ray detector
- 11: collimator
- 12: detection pixel
- 13: readout electrode
- 15: high voltage electrode
- 301: pulse output

What is claimed is:

1. An X-ray imaging apparatus comprising:

an X-ray source that irradiates an X-ray;

a photon counting detector that counts an X-ray photon for each energy bin; and an image generation unit that generates a medical image of a subject based on a detector output from the photon counting detector, wherein the X-ray imaging apparatus further comprises a control unit, and the control unit is configured to:

determine whether polarization of the photon counting detector is not stable according to an elapsed time from previous imaging; and in a case where the polarization of the photon counting detector is not stable and the subject not being present in an X-ray irradiation field which is a range where the X-ray is irradiated from the X-ray source, cause the X-ray source to irradiate the photon counting detector with the X-ray.

2. The X-ray imaging apparatus according to claim 1, wherein the control unit checks that the subject is not present in the X-ray irradiation field based on a position of a bed on which the subject is placed.

3. The X-ray imaging apparatus according to claim 1, further comprising:

a camera that images the X-ray irradiation field, wherein the control unit checks that the subject is not present in the X-ray irradiation field based on an image captured by the camera.

4. The X-ray imaging apparatus according to claim 1, wherein the control unit checks that the subject is not present in the X-ray irradiation field based on an image generated by irradiation of an X-ray dose lower than an X-ray dose in a case where the medical image is captured.

5. The X-ray imaging apparatus according to claim 1, wherein the control unit determines that the polarization of the photon counting detector is stable in a case where an elapsed time from previous imaging is shorter than a predetermined time set in advance.

6. The X-ray imaging apparatus according to claim 5, wherein the predetermined time is set in accordance with an irradiation dose.

7. An imaging method, comprising:

irradiating, by an X-ray source, an X-ray;

counting, by a photon counting detector, an X-ray photon for each energy bin;

generating, by an image generation unit, a medical image of a subject based on a detector output from the photon counting detector;

determining, by a control unit, whether polarization of the photon counting detector is not stable according to an elapsed time from previous imaging; and in a case where the polarization of the photon counting detector is not stable and the subject not being present in an X-ray irradiation field which is a range where the X-ray is irradiated from the X-ray source, causing the X-ray source to irradiate the photon counting detector with the X-ray.

8. The imaging method of claim 7, further comprising:

checking, by the control unit, that the subject is not present in the X-ray irradiation field based on a position of a bed on which the subject is placed.

9. The imaging method of claim 7, further comprising:

imaging, by a camera, the X-ray irradiation field; and checking, by the control unit, that the subject is not present in the X-ray irradiation field based on an image captured by the camera.

10. The imaging method of claim 7, further comprising:

checking, by the control unit, that the subject is not present in the X-ray irradiation field based on an image generated by irradiation of an X-ray dose lower than an X-ray dose in a case where the medical image is captured.

11. The imaging method of claim 7, further comprising:

determining, by the control unit, that the polarization of the photon counting detector is stable in a case where an elapsed time from previous imaging is shorter than a predetermined time set in advance.

* * * * *